United States Patent
Lee et al.

(10) Patent No.: US 7,005,517 B2
(45) Date of Patent: Feb. 28, 2006

(54) PARAMAGNETIC METAL-PHTHALOCYANINE COMPLEX COMPOUNDS AND CONTRAST AGENT USING THE SAME

(76) Inventors: Sung-Young Lee, A-101, Geobongheitsvilla 77-7, Younhi-dong, Seodaemun-ku, 120-824, Seoul (KR); Kyo-Im Koo, 107-1602 Hanvit Apt. 99, Eoeun-dong Yuseong-ku, 305-806 Daejon (KR)

(*) Notice: Subject to any disclaimer, the term of this patent is extended or adjusted under 35 U.S.C. 154(b) by 161 days.

(21) Appl. No.: 10/250,512
(22) PCT Filed: Jan. 4, 2002
(86) PCT No.: PCT/KR02/00012

§ 371 (c)(1),
(2), (4) Date: Nov. 17, 2003

(87) PCT Pub. No.: WO02/053570

PCT Pub. Date: Jul. 11, 2002

(65) Prior Publication Data

US 2004/0214810 A1  Oct. 28, 2004

(30) Foreign Application Priority Data

Jan. 5, 2001 (KR) .......................... 2001-555
Jan. 2, 2002 (KR) .......................... 2002-30

(51) Int. Cl.
| | |
|---|---|
| C09B 47/04 | (2006.01) |
| C07D 487/22 | (2006.01) |
| A61K 49/04 | (2006.01) |
| A61B 5/055 | (2006.01) |
| A01N 55/02 | (2006.01) |

(52) U.S. Cl. .......... 540/122; 540/128; 540/123; 540/140; 540/125; 540/139; 514/191; 514/185; 514/163; 514/410; 536/29.11; 424/9.43; 424/9.44; 424/9.3; 424/9.34; 424/9.35; 424/1.65

(58) Field of Classification Search .............. 540/122, 540/128, 123, 140, 125; 424/9.43, 9.44, 9.3, 424/9.34, 1.65; 514/191, 185, 163, 410
See application file for complete search history.

(56) References Cited

U.S. PATENT DOCUMENTS 5,622,685 A * 4/1997 Sinn et al. ............... 424/1.65

OTHER PUBLICATIONS

Saini, K.K. et al., "MnPcS4: A New MRI Contrast Enhancing Agent for Tumor Localisation in Mice", Magnetic Resonance Imaging, vol. 13, No. 7, pp. 985–990 (1995).*

* cited by examiner

Primary Examiner—Richard Raymond
Assistant Examiner—Paul V. Ward
(74) Attorney, Agent, or Firm—Nelson Mullins Riley & Scarborough, LLP (57) ABSTRACT

The present invention provides a novel paramagnetic metal-phthalocyanine complexes and pharmaceutically acceptable salts thereof, which are useful as contrast agents for MRI (Magnetic Resonance Imaging), diagnostic X-ray imaging and computed tomography(CT).

The present invention also provides contrast agents for imaging, comprising the new paramagnetic metal-phthalocyanine complexes. The new contrast agents of the present invention show high imaging enhancement effects at lower concentration and are safer than the previously reported contrast agents.

14 Claims, 6 Drawing Sheets

$^1$H NMR(CDCl$_3$, TMS) of Octa(1,4,7,10-tetraoxaundecyl) Gd-phthalocyanine, Bruker AMX 300 spectrometer is used

UV spectrum of Octa(1,4,7,10-tetraoxaundecyl) Mn-phthalocyanine, Shimadzu UV-3100S is used with 1cm matched Quartz cell at 25°C, and $CHCl_3$ as solvent

PARAMAGNETIC METAL-PHTHALOCYANINE COMPLEX COMPOUNDS AND CONTRAST AGENT USING THE SAME

CROSS REFERENCE TO RELATED PATENTS AND PATENT APPLICATIONS

The present application entered the United States as a §371 of PCT/KR02/00012, having an International Filing Date of 04 Jan. 2002, to which it claims priority, and also claims the benefit of Korean Patent Application No. 2002/0000030, having a filing date of 02 Jan. 2002, and Korean Patent Application No. 2001/0000555, having a filing date of 05 Jan. 2001, each of which is incorporated by reference herein in its entirety.

FIELD OF THE INVENTION

The present invention relates to contrast agents which are used in magnetic resonance imaging (MRI), diagnostic X-ray imaging, computed tomography (CT), etc., or more particularly, to a novel paramagnetic metal-phthalocyanine complex compound, the pharmaceutically acceptable salts thereof, and imaging contrast agents containing said compound, which further sharpen the images of organs or cellular tissues of patients when administered into patients while using MRI, etc.

BACKGROUND OF THE INVENTION

Contrast agents are mainly used to obtain images of tissues (i.e., blood vessels, tumors, etc.) and peripheral organ tissues. They are used for examining the location, size, and condition of tissues by further clarifying the brightness contrast of tumor and peripheral tissues, which have similar substituents. For distinguishing the tumor tissues from the peripheral tissues, the magnetic resonance imaging (MRI) has shown to be excellent and stable.

Many methods for examining the internal human body have been developed, and the MRI, representing the latest technology, is being increasingly used and utilized. The increase in usage is attributable to MRI's safety as compared to those of other imaging technologies. Since such methods as X-ray, CT and PET involve administrating radioactivity, which cannot be deemed completely harmless to human body, there is a disadvantage of inapplicability to patients susceptible to possible genetic mutation such as cancer patients or pregnant women. However, the MRI is a new technology, which is not restricted by radioactivity in terms of its inapplicability to certain subjects. The advantages of MRI are the facts that it shows good sensitivity to the tissues and that it does not expose patients to ionic radioactivity. Currently, MRI is being widely used in such areas as chemistry, biochemistry and medicine, and on account of its popularity, the cost of MRI has been steadily declining. Due to its short diagnostic time, the MRI is expected to gain further popularity in the future.

MRI (Magnetic Resonance Imaging) is a very advance technology, which can image brains and in vivo cellular tissues by using magnetic resonance imagining. In applying the concept that the spin of hydrogen nuclei in water, fat, etc. in vivo changes according to the applied magnetic field, the MRI is a technology which transfers the signals registered according to said changes to corresponding images. The distributions of hydrogen nuclei in water and fat are different depending on the types of tissues in vivo and also depending on the clinical conditions of the tissues. By utilizing these points and exciting the hydrogen in the area of interest, the nucleus spins are induced, and the signals thereof are measured for diagnostic purposes. The brightness of an image is affected by various variables, including the density of hydrogen, and the relaxation times ($T_1$, $T_2$) of excited hydrogen. In particular, the relaxation time ($T_1$, $T_2$) is a duration time for hydrogen to reach the original equilibrium state by way of an energy drop from the excited state (after energy absorption). These values are very important variables to the brightness contrast of an image. The smaller the values of $T_1$ and $T_2$, the greater the contrast of brightness, and through contrasting the brightness, shown as such, the internal tissues and organs could be distinguished for diagnostic purposes.

Meanwhile, these types of MRI images could be enhanced by using contrast agents. A contrast agent for MRI is a pharmaceutical preparation, which enhances the contrast of images by reducing the relaxation times of $T_1$, $T_2$, etc. of human tissues. The main types of contrast agents for MRI are products using paramagnetic or super-paramagnetic components. By using contrast agents, the signals of target organs or tissues, in part or in whole, could be amplified, or the signals of the peripheral tissues could be weakened. In this manner, the contrast of brightness could be maximized. However, due to acute toxicity of most of the paramagnetic metals, the inorganic salts of paramagnetic metals in general are not preferable as contrast agents. In order to solve this type of problems, organic chelated ligands or metal-binders are used. Organic chelated ligand, etc. form a complex with a metal, which in turn prevents free release of paramagnetic metals, and it also acts as a non-toxic carrier for paramagnetic metals, which enhances relaxation of hydrogen.

In order to use a paramagnetic metal-ligand complex as a contrast agent, there are several requirements. It needs to form a stable and hard chelate so that toxic metals are not released. Also, for easy administration to patients, it needs to have adequate water solubility and effectively enhance the relaxation rate of hydrogen ions. The efficacy thereof is generally measured in the degree of relaxation (an increase in relaxation rate per concentration (mM) of paramagnetic complex).

Gries et al. in U.S. Pat. No. 4,647,447 disclosed a complex used as a diagnostic reagent. Further, the active paramagnetic ingredient of Magnevist, which is an MRI contrast agent approved by the FDA, is a complex of diethylenetriaminepentaactic acid (DTPA) and gadolinium (III). However, the half-life period of DTPA-Gd is extremely short (about 14 minutes) so that after its administration it is rapidly washed out via urination (Hiroki Yoshikawa et al., Gazoshindan 6, 959–969 (1986)). Accordingly, with a single administration, it is difficult to make a diagnosis of various parts in the body (with respect to the site of trauma, blood vessel distribution, hemokinetic distribution, distribution amount, permeation, etc.) Further, since it is distributed non-specifically from the interior of blood vessels to the intervals of the tissue cells, there is no definite difference sometimes as between the normal tissues and the site of trauma. In these cases, a clear contrast cannot be obtained. Moreover, in the diagnostic methods using magnetic resonance imaging, the imaging time varies depending on the intensity of magnetic field of an MRI spectrometer. Hence, as for the MRI spectrometer of low magnetic field, which is widely used in general, the imaging time must be quite long. By using DTPA-Gd, which disappears from the blood vessels after a short period of time, the site of trauma cannot be examined in detail. As such, while using DTPA-Gd in diagnosis, there is a limitation according to the form of a specific site of diagnosis or a diagnostic device.

In U.S. Pat. No. 4,899,755, Lauffer and Brady disclosed a technique of synthesis of a paramagnetic metal-ligand complex for enhancing MRI with tissue-specificity to targeting tissues. This type of tissue-specific methods shows enhanced efficacy as compared to the conventional non-specific methods. In qualitative terms, a tissue-specific contrast agent confers better MR images with respect to the targeting tissues such as livers and biliaries. In quantitative terms, with a lesser amount, the tissue-specific contrast agent provides images similar to those observed by using a high-dose non-specific reagent. As such, by using a reagent specific to liver-gall, liver cancer or the malfunctions of the bilious system, which could not have been recognized (or recognized with difficulties), can now be observed.

However, the conventional paramagnetic metal-ligand complex for enhancing MRI has a problem in that it cannot be made into an appropriate pharmaceutical preparation as a contrast agent due to its low water solubility.

Meanwhile, the human blood has an osmotic pressure of 0.3 Osmol/kg-water. The conventional NMR reagents based on gadolinium (Gd) generally have a negative charge, which leads to high osmotic pressure of the water-soluble pharmaceutical preparation solutions of said reagents. For example, in case of making $Gd(DTPA)^{2-}$ into a pharmaceutical preparation for using it as 0.5M of N-methylglucamine salt in water, the osmotic pressure of the solution is 1.6~2.0 Osmol/kg-water (here, DTPA is diethylenetriaminepentaacetic acid). The contrast agent administered with such a high osmotic pressure is known to cause side effects in patients.

In light of these problems of conventional MRI contrast agents, there is an increasing demand for a superior contrast agent, having a half-life period of intermediate or long-term duration in blood, which is preferably stable with appropriate water-solubility and osmotic pressure.

Meanwhile, the X-ray contrast agents now clinically used include a variety of water-soluble iodized aromatic compounds containing 3~6 iodine atoms per molecule. These types of compounds are electrically charged (in the form of physiologically acceptable salts) or nonionic. The most popular contrast agents today are nonionic materials. Their popularity is attributable to the research finding that nonionic pharmaceutical preparations by far are more stable than ionic pharmaceutical preparations. Further, the contrast agents should take care of osmolar load to patients. In addition to water-soluble iodized pharmaceutical preparations, barium sulfates are frequently used in X-ray examination of the gastrointestinal system. A number of non-aqueous or particle pharmaceutical preparations have been proposed as non-oral X-ray contrast agents, mainly for the hepatic or lymphatic system. As examples of general particle X-ray contrast agents administered non-orally, they include suspensions of solid iodized particles, suspensions of liposomes containing aqueous iodized pharmaceutical preparations, and emulsions of iodized oils. The research and development of X-ray contrast agents has been carried out for almost 100 years, but there is a continuous demand for stabler X-ray contrast agents with superior light absorption capability.

SUMMARY OF THE INVENTION

Accordingly, the objective of the present invention lies in providing a novel compound of gadolinium-phthalocyanine and the pharmaceutically acceptable salts thereof, which are safe to human and can increase image resolution while using MRI, diagnostic X-ray imaging, computed tomography (CT), etc.

Another objective of the present invention is to provide a novel contrast agent for MRI and an X-ray contrast agent, containing said novel gadolinium-phthalocyanine, which provide enhanced resolution with a lesser amount of said novel contrast agent than that of a conventional commercialized contrast agent.

DESCRIPTION OF THE PREFERRED EMBODIMENTS

The present invention is described in detail as follows: The novel compound of the present invention is a combinant of a paramagnetic metal ion and organic ligands, or more specifically a combinant of a paramagnetic metal and substituted phthalocyanine ligands (referred to as paramagnetic metal-phthalocyanine complex compound herein).

In other words, the present invention relates to a paramagnetic metal-phthalocyanine complex of the structural formula (I) as below and the pharmaceutically acceptable salts thereof:

STRUCTURAL FORMULA (I)

A paramagnetic metal (M) in said structural formula is preferably selected from the group consisting of Gd(III), Fe(III), Mn(II and III), Cr(III), Cu(II), Dy(III), Tb(III), Ho(III), Br(III) and Eu(III). The most preferable paramagnetic metals (M) are Gd(III) and Mn(II and III), and R and $R_1$ are respectively $OCH_2CH_2OCH_2CH_2OCH_2CH_2OCH_3$.

The complex compound of the structural formula (I) and its pharmaceutically acceptable salts can be used as contrast agents for MRI. After its administration to a mammal host

(e.g., human), the contrast agent of the present invention is distributed to different types of tissues at various concentrations, absorbing magnetic frequency energy from the nuclear magnetic resonance imager. By this way, it catalyzes the relaxation of protons (within tissues) activated in water. The increase in relaxation rate of said activated protons provides other types of contrast while providing the maximum contrast when scanned using a nuclear magnetic resonance imager. The nuclear magnetic resonance imager is generally used to record images over various time frames, prior to or after the administration of said pharmaceutical preparation. There, the differences in the images produced by said pharmaceutical preparation within the tissues are used in making a diagnosis. With respect to the proton nuclear magnetic resonance imaging, for the metal (M) of said structural formula (I), paramagnetic metal-ions such as Gd(III), octahedral Mn(II), Cr(III) and Fe(III) are preferable. In particular, Gd(III) is most preferable since it has high paramagneticity, low toxicity and high instability with water.

The complex compound of the structural formula (I) of the present invention can be synthesized to a homogenous phase by way of a synthetic method well known in the field of organic chemistry. The synthesis of phthalocyanine is carried out by tetramerization of phthalonitril having a structural formula (II) as below:

STRUCTURAL FORMULA (II)

Here, R and $R_1$ respectively represent the aforementioned functional group. The synthetic method of phthalocyanine using phthalonitril is well described in such references as Phthalocyanine-Properties and Applications, Vol. 1~4, C. C. Leznoff and A. B. P. Lever, VCH Ed.

The present invention also includes a compound, in which a macromolecular carrier is conjugated to the complex compound of said structural formula (I), for enhancing its pharmaceutical characteristics. The carrier is generally selected from the group consisting of amino acid, polypeptide, protein, and polysaccharide. The phthalocyanine(I)/carrier bond can be produced as between a carbonyl group and an amine group, or as between other functional or reaction groups of prior art, such as two homo— or hetero— functional groups.

The present invention includes pharmaceutically acceptable salts of the complex compound of said structural formula (I), and includes derivatives of inorganic or organic acid and base. The acidic salts for example include acetate, adipate, alginate, aspartate, benzoate, benzene-sulfonate, bisulfate, butyrate, citrate, camphorate, camphor-sulfonate, cyclopentanepropionate, digluconate, dodecylsulfate, crown ether, etc.

Moreover, the present invention relates to a composition of a contrast agent containing said complex compound of the structural formula (I), and pharmaceutically acceptable carrier, adjuvant or vehicle. The pharmaceutically acceptable carriers, adjuvants or vehicles include but not limited to ion exchangers, alumina, aluminum stearate, lecithin, serum proteins such as human serum albumin, phosphate, glycine, sorbic acid, and buffer materials such as potassium sorbate. Moreover, the present invention may include free organic ligands or their pharmaceutically acceptable salts. It may further include free organic ligands, or calcium meglumin, sodium meglumin or their complex salts.

The complex compounds of said structural formula (I) of the present invention and the compositions of contrast agents containing said complex compound can be used as contrast agents not only for MRI, but also for diagnostic X-ray imaging and computer tomography (CT).

Moreover, the present invention relates to a method of enhancing tissue-specific contrast of MR images of organs or tissues of mammals, which comprises the step of administrating a diagnostically effective amount of a complex compound of said structural formula or a composition of a contrast agent containing said complex compound. It relates to a method of tissue-specific diagnostic X-ray imagining and computer tomography (CT) of organs or tissues of mammals, which comprises the step of administrating a diagnostically effective amount of a complex compound of said structural formula (I) or a composition of a contrast agent containing said complex compound.

When a compound according to the present invention is used as a contrast agent, its dose is determined according to the specific usage of contrast imaging diagnosis. If used for MRI diagnosis, a sterilized solution of a complex compound of said structural formula (I), which is the contrast agent of the present invention, can be administered at the concentration of 0.0001–10 mmol/kg to a mammal (e.g., human). For X-ray diagnosis, the concentration of 0.01–20 mmol/k can be administered. Generally, contrast agents are administered intravenously, but they may also be administered orally, intra-arterially or by other route.

The retention time (in blood) of the complex compound of said structural formula (I) according to the present invention is within the clinically effective range. Whereas DTPA-Gd, which is a conventional contrast agent, has a wash-out time of approximately 30 minutes, the compound of said structural formula (I) of the present invention has a wash-out time (from the tissues) of approximately 1 hour and 30 minutes. As such, since the compound of the present invention shows appropriate retention time in blood, it is possible to measure the contrast of vessel distribution (vessel tissue structure). Today, in using MR angiography, which has undergone significant advancement, a pulse sequence is required. However, the contrast agent of the present invention can contrast vessels without such pulse sequence while it is also useful as a diagnostic contrast agent for intravenous administration.

Since the compound of the present invention has good water solubility, the compound in itself can be made into a liquid preparation containing high concentration of the compound, and a solubilizer is not absolutely necessary when making it into a solution.

In addition, since the compound of the present invention is a non-ionic complex compound, it does not become ionized, in contrast to DTPA-Gd. As such, the compound of the present invention may actually reduce its total morality while making it into a solution, the result of which is to bring about reduction in osmotic pressure. The gadolinium complex according to the present invention is almost isotonic with the body fluid when made into 0.5 mol solution. Even at a concentration lower than 0.5 mol, it shows excellent effects as a contrast agent. The compound according to the present invention as such eases the load with respect to the volume in the circulation system and the balance of the body fluid after its administration in vivo, which in the end brings about results leading to safety.

The pH of the composition of the contrast agent of the present invention is approximately 6.0~6.8, or preferably 6.5~7.5. The composition of the contrast agent according to the present invention may include physiologically applicable buffers (e.g., 0.08% of NaCl physiological saline solution or TRIS(hydroxymethyl)-aminomethane) and physiologically applicable adducts (e.g., stabilizers such as paraben).

The MRI contrast agents prepared according to the method of the present invention has the following advantages as compared to the conventional contrast agents:

1. Safety

A conventional MRI contrast agent is a compound of gadolinium and DTPA and is unstable because of weak bond force between its paramagnetic metal ion and ligand. However, the phthalocyanine ligand of the present invention has a large molecular weight and a higher level of bond force with a metal ion. As such, the metal ion does not easily separate from the compound, which in turn results in substantial reduction of toxicity caused by heavy metal ions.

2. Retention Time in Tissues

Due to its small molecular weight and short half-life, the conventional MRI contrast agent is continually washed out via blood even while it may be absorbed into the cell tissues. As a consequence, the remaining amount in tissues rapidly decreases as a function of time. This leads to an excessive administration of contrast agents, and with respect to the scanning time for MRI, the conventional MRI contrast agent is disadvantageous in that the scanning has to be carried out in a short period of time due to its short retention time. However, the contrast agent of the present invention is a macromolecule, which has long retention time in cell tissues and a prolonged time period until ectosomatic wash-out. Hence, with the present invention, there is an advantage of a longer scanning period while using MRI. Moreover, the wash-out time from the tissues is prolonged therein as compared to those of the conventional contrast agents, and therefore with a lesser amount of administration, the same desirable effects of contrast could be obtained.

3. Good Solubility

A conventional MRI contrast agent containing a paramagnetic metal-ligand complex had low water solubility. As such, it was problematic in that the conventional contrast agent could not be made into an appropriate pharmaceutical preparation as a contrast agent. Since the complex compound of the structural formula (I) of the present invention has good water solubility, it is safer and is also possible to make it into a simple pharmaceutical preparation as compared to those existing contrast agents commonly administered into intravenously.

4. Economical Considerations

Since the present invention allows administration at a lesser amount as compared to the conventional contrast agents, it presents a lesser probability for exposure to heavy metal ions while reducing its production cost per unit.

By using the novel contrast agent according to the present invention, the contrast imaging diagnosis such as MRI, diagnostic X-ray, etc. can be carried out more safely and effectively.

Below, the present invention is described in further detail by way of examples. These examples are for illustrative purposes only, and the fact that the present invention is not limited by said examples whatsoever should be readily apparent to a person having ordinary skill in the art to which the invention pertains.

EXAMPLE 1

Synthesis of octa(1,4,7,10-tetraoxaundecyl)Gd-phthalocyanine 0.972 g (2.15 mmol) of 1,2-di(1,4,7,10-tetraoxaundecyl)-4,5-dicyanobenzene was dissolved in 10 ml of DMF, and 0.779 g (2.15 mmol) of oxidized gadolinium (III) was added thereto. Then, the reaction was carried out while stirring it for 12 hours at 150° C. After the reaction, the solution was filtered, and the final product was obtained by evaporating the solvent. The product obtained as such was purified with column chromatography, and 0.74 g of octa(1,4,7,10-tetraoxaundecyl)Gd-phthalocyanine was obtained thereby (yield of 69.7%). At that time, a mixed solvent of methanol and $CH_2CH_2$ at 1:5 was used for elution solvent.

Figure 1:
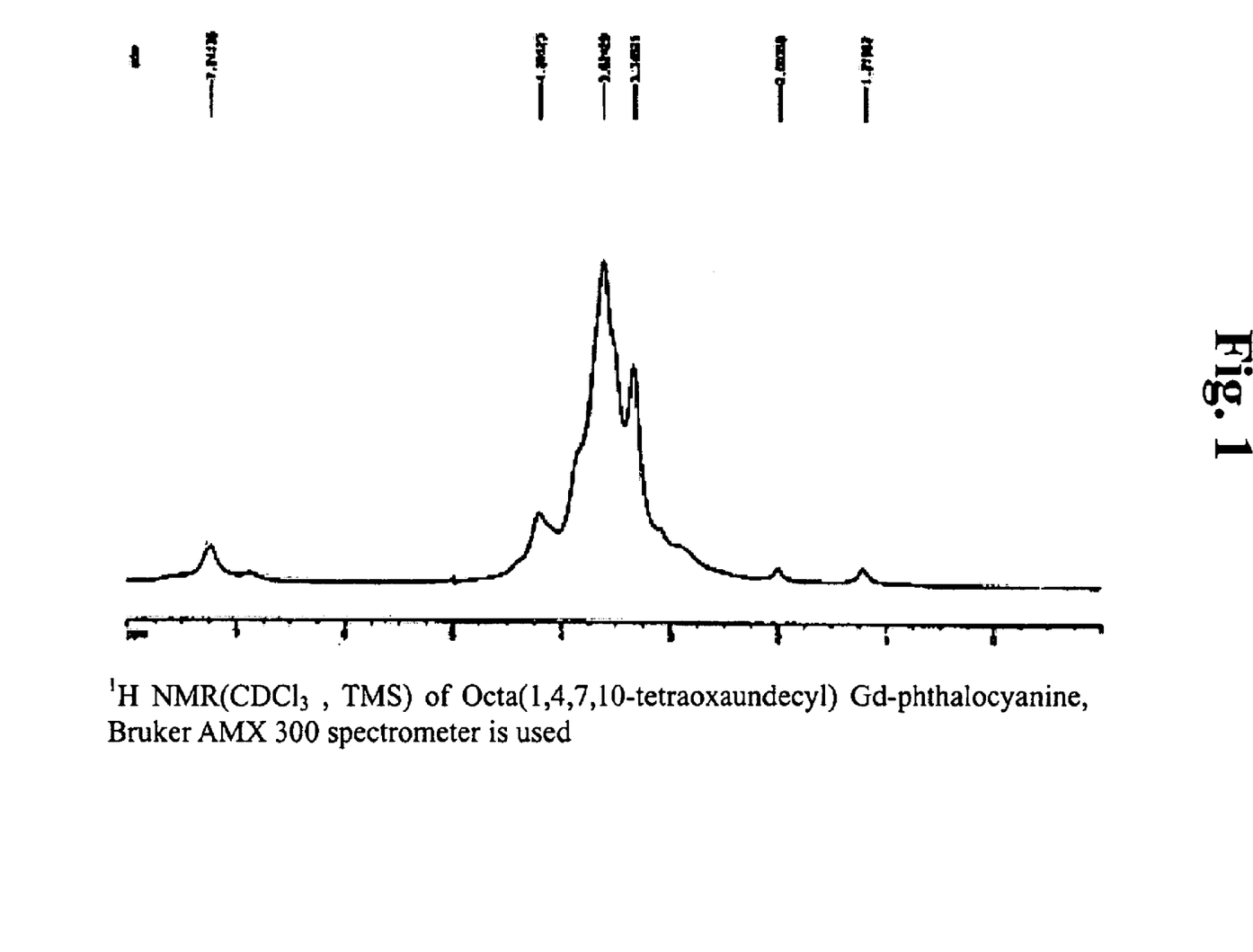
FIG. 1 is an $^1$H NMR-spectrum of octa(1,4,7,10-tetraoxaundecyl)Gd-phthalocyanine.
Figure 2:
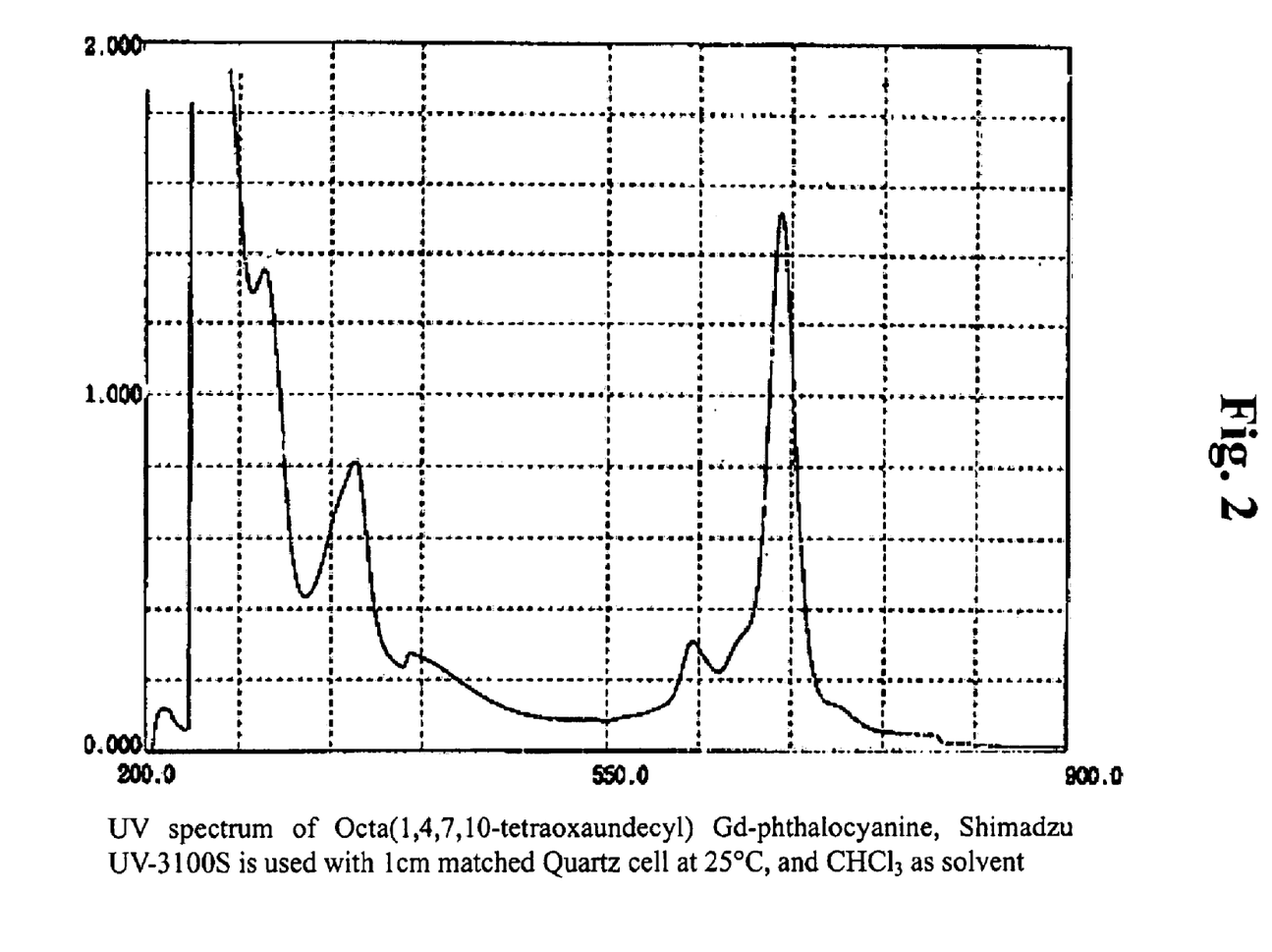
FIG. 2 is an UV-spectrum of octa(1,4,7,10-tetraoxaundecyl)Gd-phthalocyanine.

The $^1H$ NMR-spectrum and UV-spectrum of the substances obtained as such are shown respectively in FIGS. 1 and 2.

EXAMPLE 2

Synthesis of octa(14,7,10-tetraoxaundecyl)Mn-phthalocyanine 1.15 g (2.55 mmol) of 1,2-di(1,4,7,10-tetraoxaundecyl)-4,5-dicyanobenzene was dissolved in 10 ml of DMF, and 0.44 g (2.55 mmol) of $Mn(OAc)_2$ was added thereto. Then, the reaction was carried out while stirring it for 4 days at 150° C. After the reaction, the solution was filtered, and the final product was obtained by evaporating the solvent. The product obtained as such was purified with column chromatography, and 0.303 g of octa(1,4,7,10-tetraoxaundecyl)Mn-phtalocyanine was obtained thereby (yield of 25.5%). At that time, a mixed solvent of methanol and $CH_2CH_2$ at 1:5 was used for elution solvent.

Figure 3:
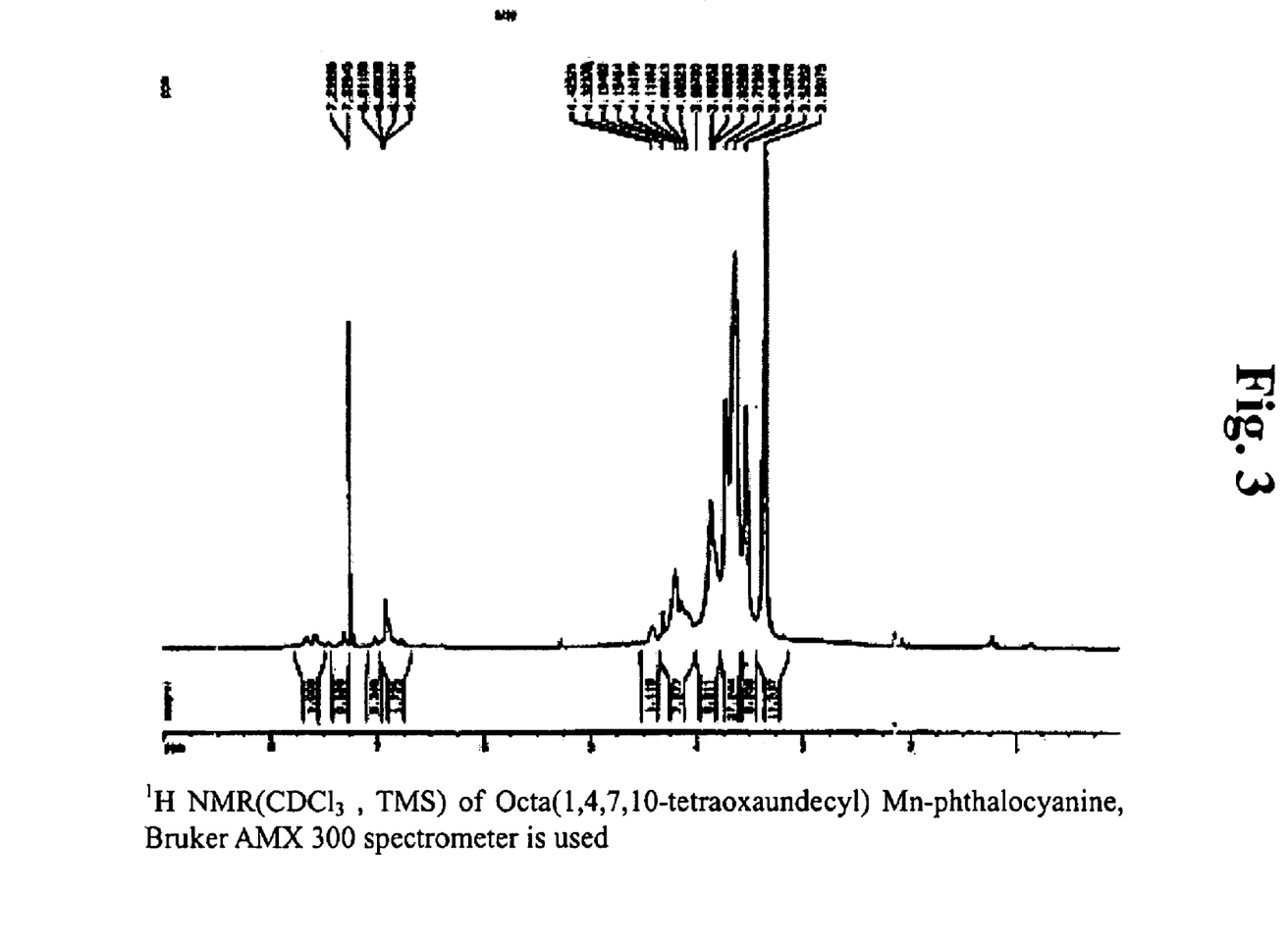
FIG. 3 is an $^1$H NMR-spectrum of octa(1,4,7,10-tetraoxaundecyl)Mn-phthalocyanine.
Figure 4:
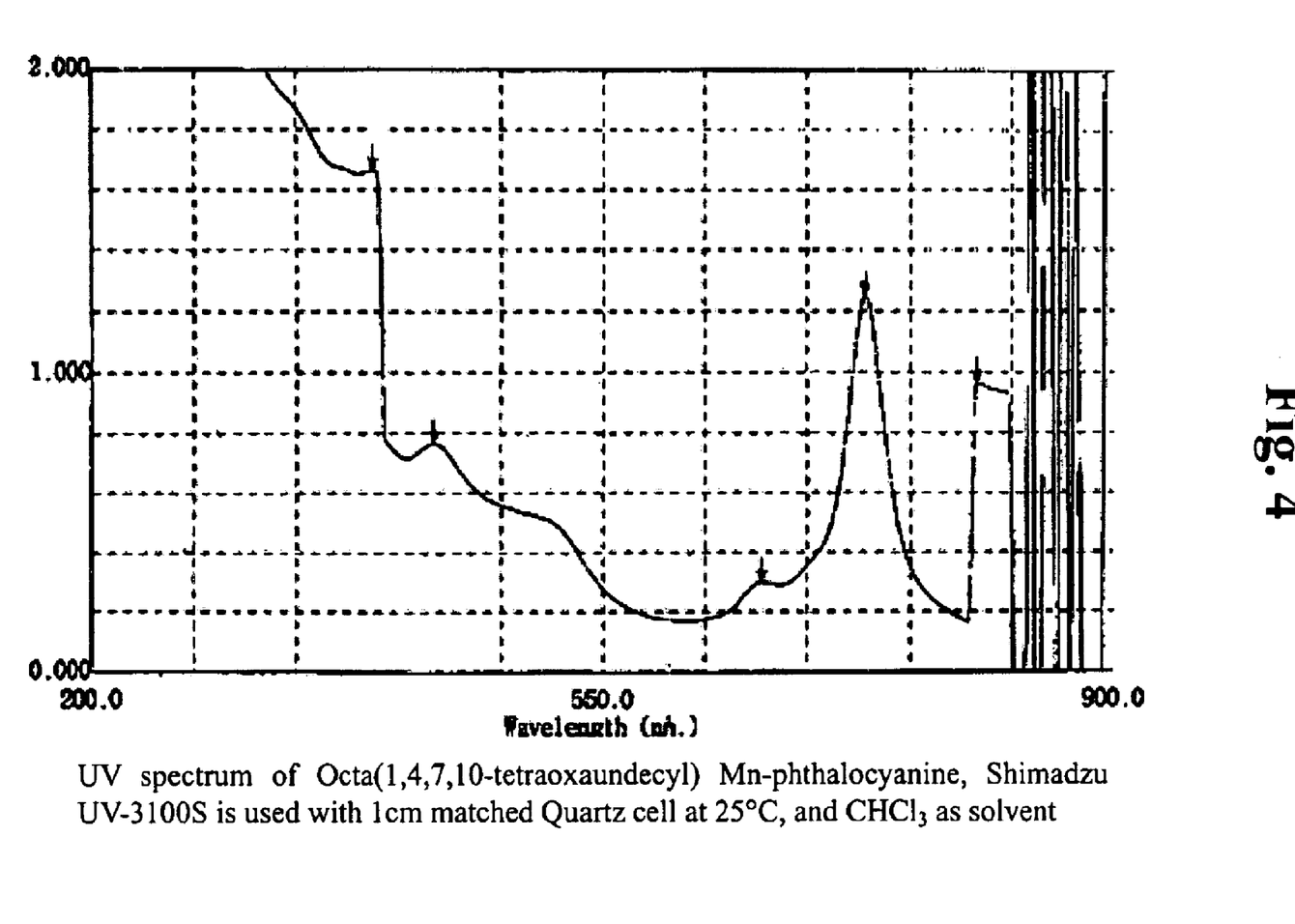
FIG. 4 is an UV-spectrum of octa(1,4,7,10-tetraoxaundecyl)Mn-phthalocyanine.

The $^1H$ NMR-spectrum and UV-spectrum of the substances obtained as such are shown respectively in FIGS. 3 and 4.

EXPERIMENT 1

$T_1$ & $T_2$ Measurements of Contrast Agents

The appropriate amounts of Gd-DTPA (a commercial contrast agent, Magnevist manufactured by Schering, Inc.), octa(1,4,7,10-tetraoxaundecyl)Gd-phthalocyanine (hereinafter referred to as GdPC-Fuxl-6) and octa(1,4,7,10- tetraoxaundecyl)Mn-phthalocyanine (hereinafter referred to as MnPC-Fuxl-18) were respectively dissolved in 0.08% physiological saline solution to produce respective samples at 0.005M concentration. To these samples, 10% of heavy water was added to obtain a lock signal. As for the blank, 0.08% physiological saline solution was prepared.

With respect to these samples and the blank, the respective relaxation times of protons were measured (values of $T_1$ and $T_2$ (unit: second)) at 80 MHz NMR (Bruker, AC80) and 300 MHz NMR (Bruker, DRX300) respectively. The respective RD values were set sufficiently high in order to eliminate their affects to the test results. The value of d2 of approximately 1~2 msec was used. The respective values of vd and vc as used were those values which were sufficient for parameter-fitting.

The relaxation times of respective samples as measured are shown in Table 1.

TABLE 1

Values of $T_1$ and $T_2$ (Unit: second)

| Samples | 80 MHz | | 300 MHz | |
|---|---|---|---|---|
| | $T_1$ | $T_2$ | $T_1$ | $T_2$ |
| 0.08% NaCl | 3.4 | 2.78 | 0.669 | 2.68 |
| Gd-DTPA | 0.0484 | 0.0441 | 0.0370 | 0.261 |
| GdPC-Fuxl-6 | 0.0243 | 0.0174 | 0.0488 | 0.0234 |
| MnPC-Fuxl-18 | 0.191 | 0.0335 | 0.317 | 0.0207 |

As shown in the results of the table, as compared to Gd-DTPA of a conventional contrast agent containing a paramagnetic metal, the compounds of GdPC-Fuxl-6 and MnPC-Fuxl-18 of the present invention showed a higher degree of relaxation of 24.3 ms/17.4 ms and 191 ms/33.5 ms (80 MHz NMR, respective $T_1/T_2$) respectively.

EXPERIMENT 2

Comparative Experiment for Contrast Imaging by Using Mouse After Administration of Contrast Agents As for the samples for obtaining magnetic resonance imaging, the appropriate amounts of Gd-DTPA (a commercial contrast agent, Magnevist manufactured by Schering, Inc.), octa(1,4,7,10-tetraoxaundecyl)Gd-phthalocyanine (hereinafter referred to as GdPC-Fuxl-6) and octa(1,4,7,10-tetraoxaundecyl)Mn-phthalocyanine (hereinafter referred to as MnPC-Fuxl-18) were dissolved in 0.08% saline solution respectively, and the respective samples at concentration of 0.01M were used. This was in reference to the administration of commercial Gd-DTPA in human at 0.5M concentration under the condition of 0.4 ml/kg in 0.2 ml.

The above contrast agents of 0.01M concentration were administrated to mouse at 0.2 ml/10 g (female ICR, 27~30 g, n=6). In the experiment, 0.4 ml/kg, which is the maximum value in the acceptable range of the dose of the contrast agent, were injected to more clearly ascertain their effects. As for the blank for comparison purposes, the solution of 0.08% NaCl was administered. After the abdominal administration of the contrast agents, followed by a thirty-minute wait, the anesthetics (solution of a mixture of rompum, ketamin, and distilled water at 1.5:1.5:7) were injected thereto in order to sufficiently penetrate the contrast agents into the abdominal organs (the images of which were to be examined). A tube was orthostatically inserted into the anestheticized mouse so that the measurement coil of the imaging probe was positioned at the abdominal cavity. The data obtained in the experiment corresponded to the images scanned at the point of time, which was 40 minutes after the administration of contrast agents. The test results of Spin-echo T intensified images after the administration of respective contrast agents are shown in FIG. 5.

Figure 5:
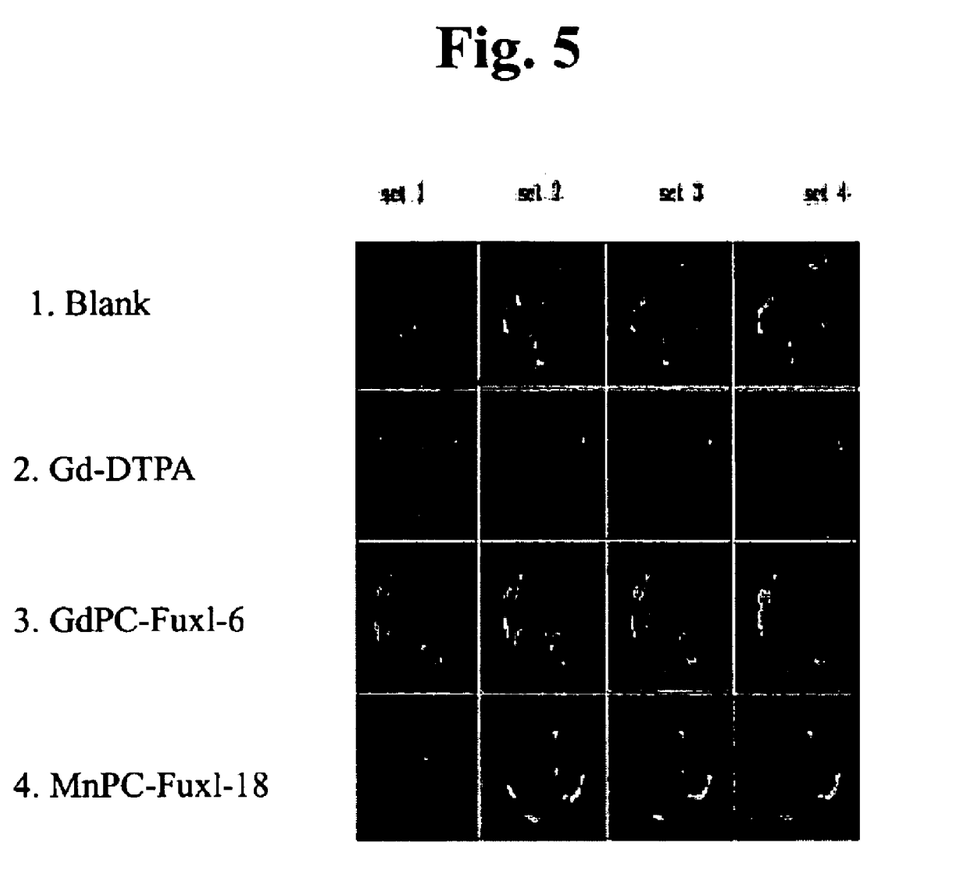
FIG. 5 shows the results of intensified imaging with respect to spin-echo T after the administration of the contrast agents according to the present invention, conventional contrast agents, and blanks to the mouse abdominal cavities.

As shown in FIG. 5, the contrast effects, respectively, were clearly shown under the condition of TE=6.46 ms, having minimized the effects of $T_2$, rather than the condition of TE=20 ms. Particularly, in comparing the $T_1$ intensified images obtained under the conditions of Set 1 and Set 2, GdPC-Fuxl-6 and MnPC-Fuxl-18 showed good contrast effects.

EXPERIMENT 3

Stability Test for Contrast Agents in Physiological Saline

After placing 0.08% physiological saline solution to two 25 ml beakers, respectively, 0.196 g of GdPC-Fuxl-6 was dissolved into one beaker, and 0.186 g of MnPC-Fuxl-18 was dissolved into the other beaker; they were made into 0.01M solution. For preventing evaporation, corks were placed onto the beakers, which in turn were heated for 24 hours in a bather at 50° C. The UV-spectrums (FIGS. 2 and 3) of GdPC-Fuxl-6 and MnPC-Fuxl-18 along with the UV-spectrum of $H_2$-phthalocyanine were compared to determine whether the separations of Gd and Mn ions had occurred therein. As a result, GdPC-Fuxl-6 and MnPC-Fuxl8 were shown to have been stabilized for 24 hours in 0.08% physiological saline (0.01M) solution at 50° C.

The conventional commercialized contrast agent, Gd-DTPA, was unstable due to weak bond force between its paramagnetic metal ion and ligand. However, as shown in the above test results, the novel paramagnetic metal-phtalocyanine complex compound according to the present invention has a large molecular weight and a higher level of bond force with the metal ion. As such, it does not easily separate from the compound, which in turn substantially reduces the toxicity caused by heavy metal ions.

EXPERIMENT 4

Light Absorption Test of GdPC-Fuxl-6

Figure 6:
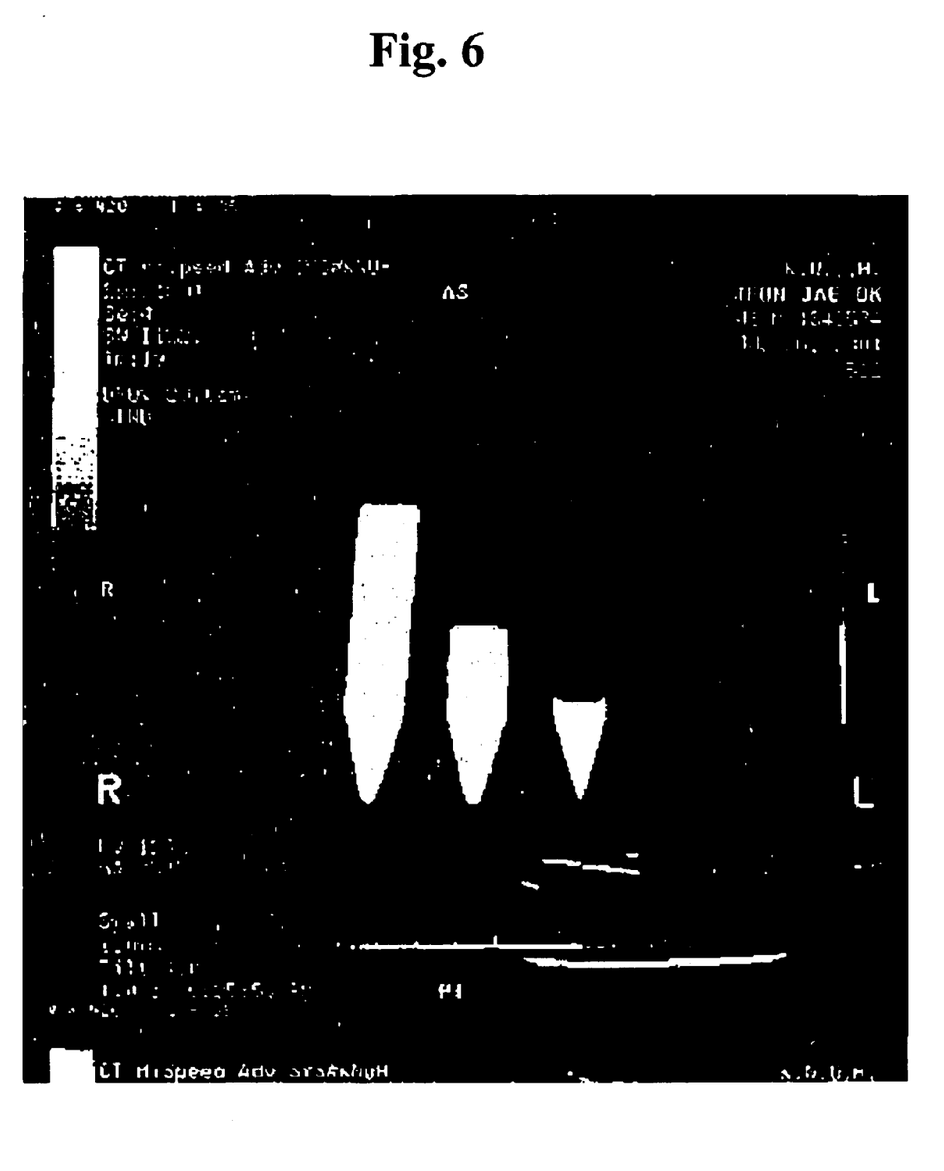
FIG. 6 shows the results of comparative measurements of light absorptions of the contrast agents according to the present invention and those of the conventional contrast agents.

The compound of the present invention, GdPC-Fuxl-6, as obtained in Example 1, and the conventional X-ray contrast agents (Iron and Super-Iron) were spread onto the sticks respectively at 2.45 mole concentration, and X-ray was irradiated thereto for comparatively measuring the degree of light absorption. The results thereof are shown in FIG. 6. FIG. 6 shows (from left) the degree of light absorption of Iron, Super-Iron, and GdPC-Fuxl-6, respectively. As shown in the test results, as compared to the conventional X-ray contrast agents (Iron and Super-Iron), the compounds of the present invention showed superior characteristics with respect to light absorption.

Industrial Applicability

As shown above, the present invention provides a novel paramagnetic-phthalocyanine complex compound, which can be used in MRI, diagnostic X-ray imaging, and computer tomography (CT). Further, as compared to the conventional commercialized contrast agents, the above contrast agent for imaging, containing said novel compound, shows enhanced resolution with a lesser amount and can be used in human in a safer manner.

What is claimed is:

1. A compound having the structural formula:

and the pharmaceutically acceptable salts thereof, wherein M is Gd(III) or Mn(II and III), and R and $R_1$ are respectively $OCH_2CH_2OCH_2CH_2OCH_2CH_2OCH_3$.

2. A compound in which the compound of claim 1 is bonded to a macromolecule selected from the group consisting of amino acid, polypeptide, protein, and polysaccharide.

3. A contrast agent for MRI, which comprises a compound of claim 2.

4. A contrast agent for diagnostic X-ray imaging or computer tomography, which comprises a compound of claim 2.

5. A composition of a contrast agent, which comprises a compound of claim 2, and pharmaceutically acceptable carrier, adjuvant, or vehicle.

6. The composition of a contrast agent according to claim 5, which further comprises free organic ligands, or their pharmaceutically acceptable salts additionally.

7. The composition of a contrast agent according to claim 5, which further comprises free organic ligands, or calcium meglumin, sodium meglumin, or their complex salts additionally.

8. A method of enhancing tissue-specific contrast of MR images of organs and tissues of a mammal, which comprises the step of administrating a diagnostically effective amount of a compound of claim 2.

9. A contrast agent for MRI, which comprises a compound of claim 1.

10. A contrast agent for diagnostic X-ray imaging or computer tomography, which comprises a compound of claim 1.

11. A composition of a contrast agent, which comprises a compound of claim 1, and pharmaceutically acceptable carrier, adjuvant, or vehicle.

12. The composition of a contrast agent according to claim 11, which further comprises free organic ligands, or their pharmaceutically acceptable salts additionally.

13. The composition of a contrast agent according to claim 11, which further comprises free organic ligands, or calcium meglumin, sodium meglumin, or their complex salts additionally.

14. A method of enhancing tissue-specific contrast of MR images of organs and tissues of a mammal, which comprises the step of administrating a diagnostically effective amount of a compound of claim 1.

* * * * *